US012223093B2

United States Patent
Yousfi et al.

(10) Patent No.: US 12,223,093 B2
(45) Date of Patent: *Feb. 11, 2025

(54) SYSTEMS AND METHODS FOR PROCESSING ELECTRONIC IMAGES ACROSS REGIONS

(71) Applicant: HeartFlow, Inc., Mountain View, CA (US)

(72) Inventors: Razik Yousfi, Brooklyn, NY (US); Leo Grady, Darien, CT (US); Nathalie D'Amours, Redwood City, CA (US)

(73) Assignee: HeartFlow, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/585,295

(22) Filed: Feb. 23, 2024

(65) Prior Publication Data
US 2024/0232433 A1 Jul. 11, 2024

Related U.S. Application Data

(63) Continuation of application No. 17/466,312, filed on Sep. 3, 2021, now Pat. No. 11,941,152, which is a
(Continued)

(51) Int. Cl.
*G06F 21/62* (2013.01)
*G16H 10/60* (2018.01)

(52) U.S. Cl.
CPC ......... *G06F 21/6254* (2013.01); *G16H 10/60* (2018.01)

(58) Field of Classification Search
None
See application file for complete search history.

(56) References Cited

U.S. PATENT DOCUMENTS

2005/0236474 A1  10/2005  Onuma et al.
2006/0026040 A1   2/2006  Reeves et al.
(Continued)

FOREIGN PATENT DOCUMENTS

CN   103270513 A   8/2013
CN   104680076 A   6/2015
(Continued)

OTHER PUBLICATIONS

Garfinkel, Simson. "De-identification of Personal Information." US Department of Commerce, National Institute of Standards and Technology, Oct. 2015, pp. 1-54.
(Continued)

*Primary Examiner* — Stella Higgs
(74) *Attorney, Agent, or Firm* — Bookoff McAndrews, PLLC

(57) ABSTRACT

Systems and methods are disclosed for preserving patient privacy while transmitting health data from one geographic region to another geographic region for data analysis. One method includes receiving patient-specific health data including patient privacy information at a first region; removing the patient privacy information from the patient-specific health data to generate anonymous health data; storing the patient privacy information at the first region; and transmitting the anonymous health data to a second region for analysis.

20 Claims, 9 Drawing Sheets

Related U.S. Application Data continuation of application No. 15/635,127, filed on Jun. 27, 2017, now Pat. No. 11,138,337.

(60) Provisional application No. 62/355,742, filed on Jun. 28, 2016.

(56) References Cited

U.S. PATENT DOCUMENTS

| | | |
|---|---|---|
| 2006/0179073 A1 | 8/2006 | Kimura |
| 2007/0294110 A1 | 12/2007 | Settimi |
| 2008/0147554 A1 | 6/2008 | Stevens et al. |
| 2010/0034376 A1 | 2/2010 | Okuizumi et al. |
| 2011/0153351 A1 | 6/2011 | Vesper et al. |
| 2012/0041739 A1 | 2/2012 | Taylor |
| 2012/0053918 A1* | 3/2012 | Taylor .................. G16H 50/50 703/9 |
| 2013/0208966 A1 | 8/2013 | Zhao et al. |
| 2015/0128284 A1 | 5/2015 | LaFever et al. |
| 2015/0149208 A1 | 5/2015 | Lynch et al. |
| 2015/0342537 A1 | 12/2015 | Taylor et al. |
| 2016/0014817 A1 | 1/2016 | Cave et al. |
| 2016/0147945 A1 | 5/2016 | MacCarthy et al. |
| 2016/0148017 A1 | 5/2016 | Gossler et al. |
| 2016/0154977 A1 | 6/2016 | Jagadish et al. |
| 2016/0224805 A1 | 8/2016 | Patti |
| 2019/0272898 A1* | 9/2019 | Dormer .................. G16H 30/20 |

FOREIGN PATENT DOCUMENTS

| | | |
|---|---|---|
| JP | 2004008304 A | 1/2004 |
| JP | 2007241589 A | 9/2007 |
| JP | 2007531124 A | 11/2007 |
| JP | 2008117365 A | 5/2008 |
| JP | 2015219371 A | 12/2015 |
| KR | 1020100001730 A | 1/2010 |
| WO | 2008069011 A1 | 6/2008 |
| WO | 2016042356 A1 | 3/2016 |

OTHER PUBLICATIONS

Oshima, Mari, "Vessel Shape Modeling and Blood Flow Analysis From Medical Images of Cerebral Aneurysm", BME, Japanese Society for Medical and Biological Engineering.

Rita Noumeir et al: "Pseudonymization of Radiology Data for Research Purposes", Journal of Digital Imaging; The Journal of the Society for Computer Applications in Radiology, vol. 20, No. 3, Dec. 28, 2006, pp. 284-295.

* cited by examiner

SYSTEMS AND METHODS FOR PROCESSING ELECTRONIC IMAGES ACROSS REGIONS

RELATED APPLICATION(S)

This patent application is a continuation of U.S. application Ser. No. 17/466,312 filed Sep. 3, 2021, which in turn is a continuation of U.S. application Ser. No. 15/635,127 filed Jun. 27, 2017, which claims benefit of priority to U.S. Provisional Application No. 62/355,742 filed Jun. 28, 2016, each of which are incorporated herein by reference in their entireties.

INTRODUCTION

Various countries or geographic regions may possess different requirements for protecting patient privacy. Such requirements may limit or prevent transfer of health data or health information across borders. For example, United States law seeks to protect patient privacy by defining a category of information that can link an individual's health information to the individual. This category of information is called, "protected health information (PHI)", and U.S. medical professionals and service providers (e.g., doctors, hospitals, insurance companies, covered entities, business associates, etc.) are governed by regulations that dictate usage and transfer of PHI-associated data. Other countries and regions may include analogous regulations, laws, and/or standards. For example, Canada protects patient information at the federal and at the provincial level. As another example, Europe will protect personal data (including medical information) under the General Data Protection Regulation (GDPR) starting on May 25, 2018.

At the same time, particular data analysis capabilities may exist only within a certain region. For example, a particular medical company may have data analysis facilities only in one selected region. Patients outside of that selected region may not have access to the company's data analysis services, since patient privacy regulations may dictate that their health data cannot be transferred to the selected region. Patient access to various medical analyses may be limited due to patient privacy regulations, and data analysis companies may be prevented from serving patient bases from various regions. In short, patient privacy regulations limiting cross-border transfer of patient privacy information may mean that data cannot be analyzed by data analysis facilities that exist out of region. Consequently, patients may be limited to data analysis capabilities available within their regions. Furthermore, data analysis companies may have to maintain facilities for each region governed by a particular set of patient privacy regulations, in order to service patients of that region.

A desire thus exists for preserving patient privacy, while still permitting data collected in one region to be analyzed in a second region. The foregoing general description and the following detailed description are exemplary and explanatory only and are not restrictive of the disclosure. Various embodiments of the present disclosure relate to systems and methods of preserving patient privacy while transmitting health data from one geographic region to another geographic region for data analysis, according to one embodiment.

SUMMARY

According to certain aspects of the present disclosure, systems and methods are disclosed for permitting transmission and analysis of health data between regions, while preserving patient privacy.

One method includes receiving patient-specific health data including patient privacy information at a first region; removing the patient privacy information from the patient-specific health data to generate anonymous health data; storing the patient privacy information at the first region; and transmitting the anonymous health data to a second region for analysis.

In accordance with another embodiment, a system for providing cross-border health data transfer while preserving patient privacy comprises: a data storage device storing instructions for providing cross-border health data transfer while preserving patient privacy; and a processor configured for: receiving patient-specific health data including patient privacy information at a first region; removing the patient privacy information from the patient-specific health data to generate anonymous health data; storing the patient privacy information at the first region; and transmitting the anonymous health data to a second region for analysis.

In accordance with another embodiment, a non-transitory computer readable medium for use on a computer system containing computer-executable programming instructions for performing a method of providing cross-border health data transfer while preserving patient privacy, the method comprising: receiving patient-specific health data including patient privacy information at a first region; removing the patient privacy information from the patient-specific health data to generate anonymous health data; storing the patient privacy information at the first region; and transmitting the anonymous health data to a second region for analysis.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments, and together with the description, serve to explain the principles of the disclosed embodiments.

Figure 1:
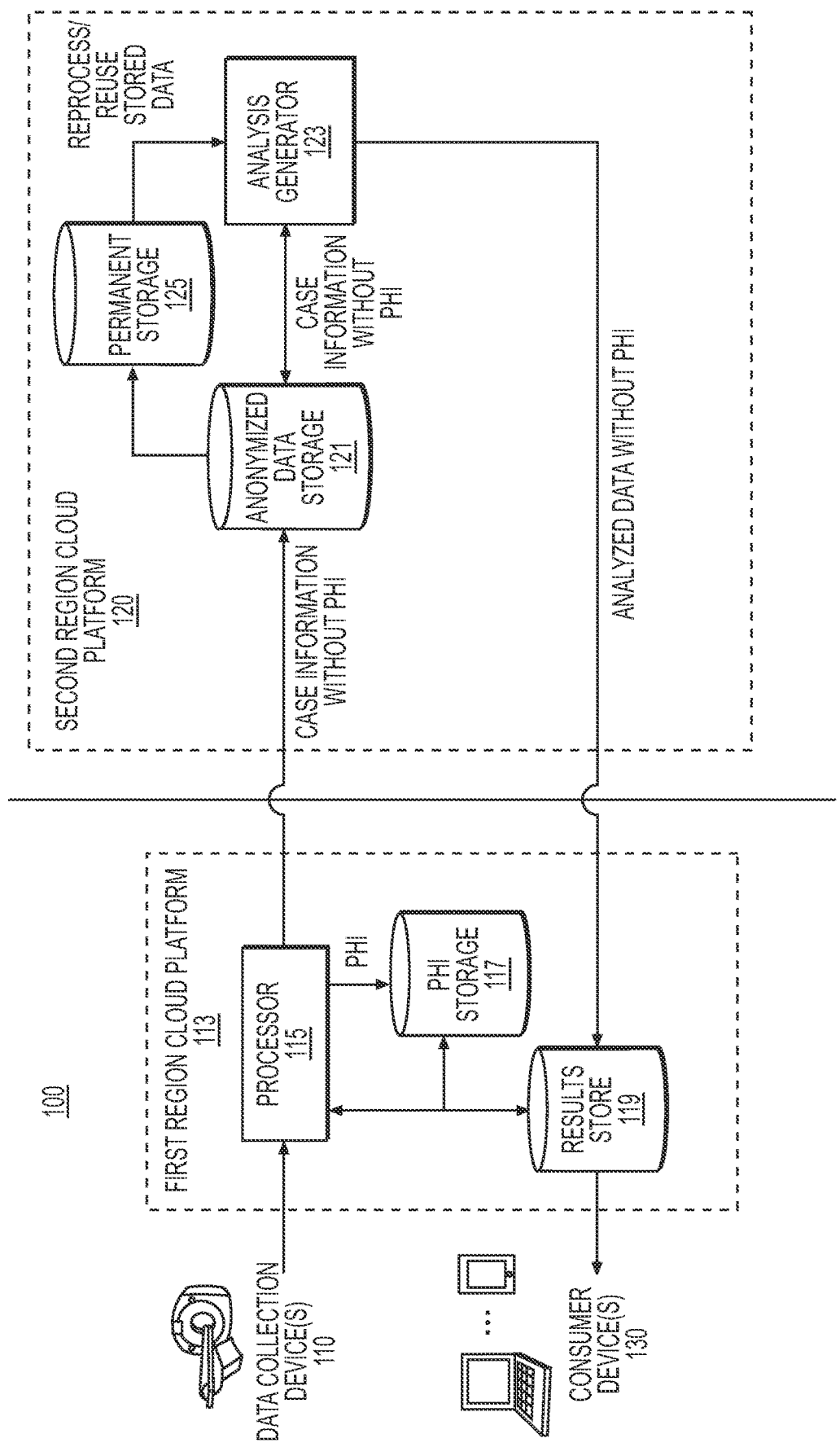
FIG. 1 is an exemplary schematic block diagram of a cross-border data system for transmitting health data via cloud platforms, according to an exemplary embodiment of the present disclosure.

As used herein, the term "exemplary" is used in the sense of "example," rather than "ideal." In addition, the terms "first," "second," and the like, herein do not denote any order, quantity, or importance, but rather are used to distinguish one concept or structure from another. Moreover, the terms "a" and "an" herein do not denote a limitation of quantity, but rather denote the presence of one or more of the referenced items. For the purposes of the disclosure, "patient" may refer to any individual or person for whom diagnosis or treatment analysis (e.g., data analysis) is being performed, or any individual or person associated with the diagnosis or treatment analysis of one or more individuals.

The term, "health data" may include medical data collected for a patient in one practice, as well as health data collected for the patient by any health care providers, labs, specialists, clinicians, etc. Health data may be associated with a particular patient, where the patient is identifiable via patient privacy information. Patient privacy information may be any information that links health data to a particular individual. Patient privacy information may be defined objectively (as information that ties an individual to his/her health data) and/or by laws and regulations. Various regions may include different definitions of what information that constitutes patient privacy information. "Region" may refer to any environment with borders defined by regulations protecting patient privacy. In one embodiment, "region" may refer to a known geographic region governed by a set of regulations that protect patient privacy/personal data. For example, "region" may refer to a state (e.g., California), a country (e.g., the United States, Japan, Canada, etc.), or a group of countries (e.g., Europe) operating under a single set of patient privacy laws. For the United States, patient privacy information may include protected health information (PHI). For the United States and various other regions, patient privacy information may include personal health information, patient identification information, etc.

Alternately or in addition, "region" may refer to a given physical facility, a given entity's computing systems, or a given cloud platform. In such cases, various regions between which health data is redacted may nevertheless exist within a single country, state, or province. For example, a first region may include a hospital that may remove patient privacy information from collected health data prior to transferring the health data to a second region (e.g., a cloud platform) for data analysis. The hospital and the cloud platform may exist in the same geographically defined region, e.g., the United States.

DESCRIPTION OF THE EMBODIMENTS

Reference will now be made in detail to the exemplary embodiments of the disclosure, examples of which are illustrated in the accompanying drawings. Wherever possible, the same reference numbers will be used throughout the drawings to refer to the same or like parts.

The present disclosure includes a system and method for permitting transmission and analysis of health data between regions, while preserving patient privacy. In one embodiment, health data generated in one region may be stripped of patient privacy information and transmitted to a second region. The health data may be analyzed in the second region, and then analyzed data may be transferred from the second region to the first region where it is coupled to its respective patient privacy information. In this way, data analysis may be performed in a remote region, without transmitting patient privacy information to the remote region. In this way, transmission of health data may include modifying and redacting health data so that the data may undergo analysis at a remote region.

In one embodiment, a cloud platform in a first region may receive health data. The health data may include patient case/health information with or without patient privacy information. The health data may include data produced, generated, or received at a first region. For example, health data may include image data generated from one or more imaging modalities (e.g., CT, MRI, ultrasound, etc.).

In one embodiment, the health data may be decoupled from patient privacy information at the first region. For example, the health data may be decoupled from patient privacy information prior to the health data being transmitted from the first region to a second region. The first region's cloud platform may strip any detected patient privacy information from the received health data, and store the patient privacy information via any storage medium. For instance, the first region's cloud platform may receive health data files of CT scans, where the CT scans are associated with PHI. For this scenario, the first region's cloud platform may strip the received CT scans of PHI and store the PHI. The PHI may be stored in a PHI storage system (e.g., a PHI database).

The first region's cloud platform may communicate with a cloud platform at a second region. For example, the first region's cloud platform may transmit anonymized health data (e.g., health data without patient privacy information) to the cloud platform at the second region. In other words, the health data may be transferred to the second region while its associated patient privacy information remains exclusively within the first region. In one embodiment, the first region's cloud platform may receive a data analysis request associated with the received health data file. The first region's cloud platform may identify that the requested data analysis should be performed at a second region. The first region's cloud platform may then communicate with a cloud platform at the second region to prompt the second region's cloud platform to complete the requested data analysis. In one embodiment, the second region may notify the first region when data analysis is complete, or when analyzed data is available for re-identification.

In one embodiment, data analysis may be performed at the second region. For instance, reports of analyzed data may be generated at the second region. In one scenario, the cloud platform at the second region may receive anonymized health data, generate an anonymous report of analyzed data, and transmit the anonymous report to the cloud platform at the first region. For example, the report may comprise a portable document format (PDF) file of one or more metrics, graphics, images, treatment recommendations, etc. derived from data analysis performed on the anonymized health data. Alternately or in addition, the report may include a file that may provide various interactive interface(s) to a user, including e.g., anatomical model(s), comparison(s) to population data, prediction(s), simulation(s) (e.g., of treatment effects, fluid flow, heat transfer, etc.), treatment recommendations, etc.

In one embodiment, the first region cloud platform may receive an anonymous report and match the report to a patient. For example, the anonymous report may be associated with an identifier that corresponds to patient privacy information corresponding to patient privacy information stored in the first region cloud platform.

In one embodiment, the first region cloud platform may tag the patient health data with an identifier unrelated to patient privacy. The identifier may be random, not data-specific, and/or associated with a region, time/date, hospital, etc. The identifier may be used to track the patient data in the absence of patient privacy information, since the data may be decoupled from patient privacy information prior to being transferred out of the first region. In one embodiment, a cloud platform at the first region may include a database of stored patient privacy information, e.g., a PHI database. Once reports of analyzed health data are transferred to the first cloud platform and the first region, the first cloud platform may match the identifier to stored patient privacy information (e.g., stored PHI of a PHI database).

In one embodiment, patient privacy information may be encrypted in every iteration of its use and existence within the described systems and methods. For example, patient privacy information may be encrypted in transit (e.g., transmission within a region, transmission to storage, removal from storage, etc.), at rest (e.g., in storage, sorting, during data collection, etc.), or during reattachment to analyzed data, etc. For instance, PHI may be encrypted when it is received with patient health data. PHI may further be encrypted when it is moved over an encrypted link (e.g., Secure Sockets Layer (SSL). SSL may provide increased security over a network. PHI may also be encrypted when sorting prior to storage, and (again) be encrypted when it is stored. For example, PHI may be stored at a location (e.g., a database) that may be encrypted. One or more keys to the storage location may be securely stored, so that even if the storage location is known, the stored contents may be encrypted and inaccessible. PHI may further be encrypted when it is retrieved from a database and/or used to generate new reports. In a further embodiment, all data transmitted within the disclosed system (e.g., patient privacy information, health data, stored data, analyzed data, identifiers, hashes, etc.) may be encrypted.

Alternately or in addition, hashes of patient privacy information may be generated or used to anonymously link patient privacy information to an identifier. For example, a selected patient's patient privacy information serve as input for a hash function, and the hash function may output a hash. The hash may be mapped to the input patient privacy information, even if the hash does not include patient privacy information. In one embodiment, the hash function may be an irreversible hash function that may omit patient privacy information. Exemplary hash functions include SHA1, MD5, bcrypt, etc. Any hash function may be used, but the same hash algorithm may be used on each case, so that different data sets may be mapped to one another. In one embodiment, hashes may include unique values computed for each of the fields considered patient privacy data. Any field of the patient privacy information may be hashed. Exemplary hashed fields may include: patient's first name, patient's last name, a patient identifier (e.g., patient ID), a patient's date of birth, a referring physician's first name, a referring physician's last name, a study date, a study time, etc.

In one embodiment of hash usage, PHI may be stored in a PHI database exclusively in a first region (e.g., the United States). Hashes may be stored alongside the identifier associated with PHI and/or patient health data. Hashes may also be sent to or stored in permanent storage of the second region. Hashes may provide ways to track a health data longitudinally at the second region, absent patient privacy information. In other words, the hash may allow data to be linked to another piece of data. In one exemplary instance of hash usage, a first platform in a first region may receive a first scan. The first scan may be a medical scan of a patient, John Doe. The first platform may store hashes for "John" and "Doe." At another time, a different scan may be received, also for John Doe. The first cloud platform may hash again this received scan for John Doe and compare the second hash to the stored hashes. Since the second hash for the different scan may match the stored hashes for "John" and "Doe," the first region cloud platform may conclude that the scans belong to the same patient (e.g., John Doe).

In one embodiment, hashes may be generated and stored by the region creating and pushing a case. In one embodiment, hashes may be transmitted between regions, while patient privacy information remains in the region in which patient health data was collected. Alternately or in addition, hashes may be computed when anonymized health data is in transit to a second region, prior to data analysis.

Any cloud platforms may use the hashes to relate data sets to each other as likely being associated with a particular individual, but only the cloud platform where the health data was originally collected can connect a hash to patient privacy information. Hashes or identifiers may permit tracking of health data without transferring patient privacy information across borders.

Figure 2:
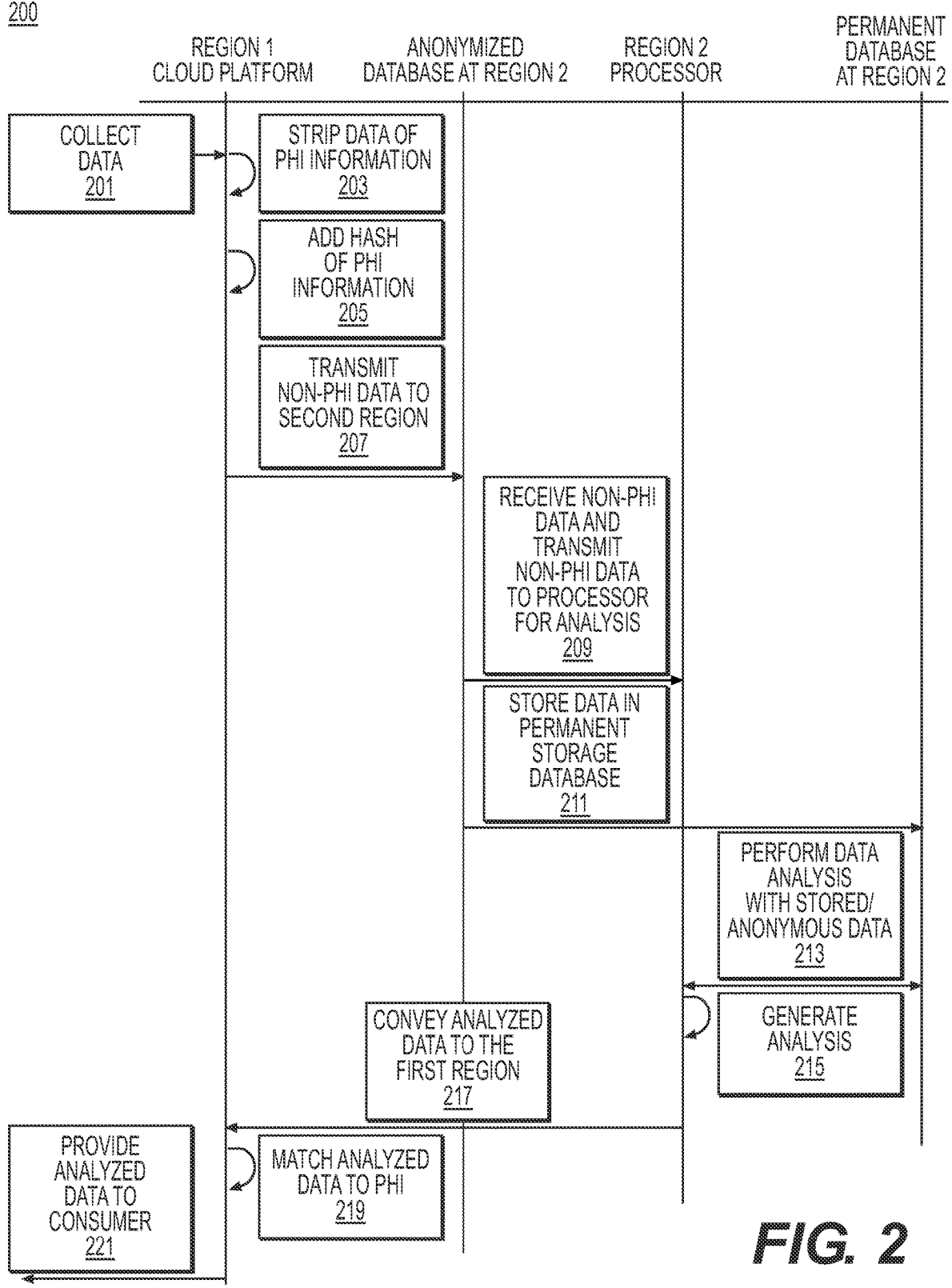
FIG. 2 is a flow diagram of an exemplary method of transmitting health data via cloud platforms of different regions, according to an exemplary embodiment of the present disclosure.

FIG. 1 is a schematic of a cross-border data system of transferring health data between a first region and a second region. FIG. 2 is a flow diagram of an exemplary process of health data transfer between the first region and the second region. FIGS. 3A-3D depict general embodiments of systems and methods at an exemplary "first region," collecting health data and storing patient privacy information respective to the collected health data. FIGS. 4A-4C depict general embodiments of systems and methods at an exemplary "second region," where analysis of anonymized health data may take place. For clarity, FIGS. 1-4C show the "first region" as the privacy preservation region and the "second region" as the data analysis region.

In practice, a geographic region may be both a privacy preservation region and an analysis region, with the primary goal being that patient privacy information stays in the region where the health data is generated. For example, data may be generated in Europe (e.g., region 1). This data may be stripped of patient privacy information and transmitted to the United States (e.g., region 2) for analysis. A United States cloud platform may generate analyzed data and transmit the analyzed data back to Europe, where a cloud platform may receive the analyzed data and pair the analyzed data with its corresponding patient privacy information. At the same time, a European cloud platform may be receiving raw health data stripped of PHI from the US, analyzing that health data, and transmitting analyzed data to the U.S. where it will be coupled to its respective PHI stored in the U.S. While the embodiments show designated roles for a "first region" and a "second region," it would be understood by one of ordinary skill in the art that a geographic region may possess or provide both "first region" and "second region" capabilities.

Furthermore, while the present embodiments describe example scenarios that include two (2) geographical or geopolitical regions (e.g., the first region and the second region being different countries), the disclosed systems and methods may include embodiments comprising any number of, e.g., several various or various types of regions where patient privacy information may be removed, retained, and used to be reattached onto received, analyzed data, as well as several regions where anonymous health data may be received and processed. Within such a system, some regions-to-region interaction may not necessarily trigger removal of PHI information as a precursor to transmitting data between the regions, while other regions within the same system may exchange data only after patient privacy information regulation compliance is met.

FIG. 1 is an example schematic block diagram of a cross-border data system 100 for transmitting health data via cloud platforms, according to an exemplary embodiment of the present disclosure. Cross-border data system 100 may comprise multiple computing systems and/or devices configured to send and receive information from data collection device(s) 110, a cloud platform of a first region 113, a cloud platform of a second region 120, and consumer device(s) 130 over an electronic network. In one embodiment, first region cloud platform 113 may serve as a data privacy platform (collecting and preparing data for securing patient privacy) while the second region cloud platform 120 may serve as a data analysis platform. In one embodiment, various components of each cloud platform 113 or cloud platform 120 may be in direct local contact with one or more other components of the cross-border data system 100. In one embodiment, cross-border data system 100 may operate over a wide area network (WAN) or local area network (LAN), with various components of cross-border data system 100 running remotely or independently from one another.

It should be appreciated that cross-border data system 100 may include any type or combination of computing systems, e.g., handheld devices, personal computers, servers, clustered computing machines, and/or cloud computing systems. In one embodiment, cross-border data system 100 may comprise an assembly of hardware, including a memory, a central processing unit ("CPU"), and/or a user interface. The memory may include any type of RAM or ROM embodied in a physical storage medium, such as magnetic storage including floppy disk, hard disk, or magnetic tape; semiconductor storage such as solid state disk (SSD) or flash memory; optical disc storage; or magneto-optical disc storage. The CPU may include one or more processors for processing data according to instructions stored in the memory. The functions of the processor may be provided by a single dedicated processor or by a plurality of processors. Moreover, the processor may include, without limitation, digital signal processor (DSP) hardware, or any other hardware capable of executing software. The one or more user interfaces may include any type or combination of input/output devices, including a display monitor, touchpad, touchscreen, microphone, camera, keyboard, and/or mouse, or other interface. Each region of the cross-border data system 100 may include such an assembly of components, as described in further detail below.

In one embodiment, data collection device(s) 110 may generate or receive health data. For example, health data may include patient-specific image data (e.g., Digital Imaging and Communications in Medicine (DICOM) files). In one scenario, image data may include data regarding the geometry of the patient's heart, e.g., at least a portion of the patient's aorta, a proximal portion of the main coronary arteries (and the branches extending therefrom) connected to the aorta, and the myocardium. The patient-specific anatomical data may be obtained noninvasively, e.g., using a noninvasive imaging method. For example, CCTA is an imaging method in which a user may operate a computer tomography (CT) scanner to view and create images of structures, e.g., the myocardium, the aorta, the main coronary arteries, and other blood vessels connected thereto. The CCTA data may be time-varying, e.g., to show changes in vessel shape over a cardiac cycle. CCTA may be used to produce an image of the patient's heart.

Alternatively, other noninvasive imaging methods, including magnetic resonance imaging (MRI) or ultrasound (US), or invasive imaging methods, such as digital subtraction angiography (DSA), may be used to produce images of structures of a patient's anatomy. The imaging methods may involve injecting the patient intravenously with a contrast agent to enable identification of the structures of the anatomy. The resulting imaging data (e.g., provided by CCTA, MRI, etc.) may be provided by a third-party vendor, such as a radiology lab or a cardiologist, by the patient's physician, etc.

Other patient-specific anatomical data may also be determined from the patient noninvasively. For example, physiological data such as the patient's blood pressure, baseline heart rate, height, weight, hematocrit, stroke volume, etc., may be measured. The blood pressure may be the blood pressure in the patient's brachial artery (e.g., using a pressure cuff), such as the maximum (systolic) and minimum (diastolic) pressures. Exemplary data collection device(s) 110 may thus include imaging modalities, wearables, blood pressure cuffs, thermometers, fitness trackers, glucometers, heart rate monitors, etc.

In one embodiment, the health data may be received at a first region cloud platform 113. The first region cloud platform 113 may have two functions: (1) preparing collected health data for analysis at a second region, and (2) matching analyzed data received from the second region with patient privacy information stored in the first region. For the first function, the first region cloud platform 113 may remove patient privacy information associated with the collected health data. For the second function, the first region cloud platform 113 may receive analyzed data from a second region, where the analyzed data is stripped of any patient privacy information. The first region cloud platform 113 may identify which patient is associated with the received analyzed data, and provide access to the analyzed data by consumer device(s) 130. It is understood that the first region cloud platform may reside in any region and the patient privacy information may correspond to the patient privacy regulations and standards of that respective first region. For illustration, the exemplary first region cloud platform 113 may be located in the United States, where patient privacy information may be comprised of PHI.

The first region cloud platform 113 may be comprised of various components including a processor 115, PHI storage 117, and a results store 119. In one embodiment, processor 115 may receive collected data within the first region. The patient-specific anatomical data obtained (e.g., by data collection device(s) 110) may be transferred over a secure communication line (e.g., via a network). For example, the data may be transferred to a server or other computer system. In an exemplary embodiment, the data may be transferred to a server or other computer system operated by a service provider providing a web-based service, e.g., cloud platform 113. Alternatively, the data may be transferred to a computer system operated by the patient's physician or other user, e.g., for analysis, viewing, or storage within the first region.

In an exemplary embodiment where patient privacy information comprises PHI, processor 115 may further strip the collected health data of PHI. For example, processor 115 may decouple health data from associated PHI and store the PHI (e.g., using PHI storage 117). In one embodiment, processor 115 may further create one or more hashes of the PHI, where the one or more hashes do not contain PHI. The hashes may be irreversible. Processor 115 may transmit the data to a second region, such that the data is transferred with the one or more hashes, but without PHI. The PHI may remain within the first region. In one embodiment, the results store 119 may be accessed at a later stage, when analyzed data from a second region enters the first region. For example, results store 119 may store analyzed data from the second region.

In one embodiment, processor 115 may transmit anonymized health data to a second region cloud platform 120. In one embodiment, cloud platform 120 may include an anonymized data storage 121, analysis generator 123, and permanent storage 125. In one embodiment, anonymized data storage 121 may be comprised of various data decoupled from patient privacy information (e.g., PHI). Anonymized data storage 121 may receive and/or store any data files arriving from regions other than the second region. For example, anonymized data storage 121 may include storage for anonymous DICOM data sets, analyzed data reports, various auxiliary data, etc. In one embodiment, data stored in the anonymized data storage 121 may be analyzed by analysis generator 123. Analysis generator may perform any form of data analysis based on data of anonymized data storage 121. An exemplary form of data analysis may include noninvasive determinations of patient-specific blood flow characteristics and/or simulations of blood flow. Various systems and methods of such blood flow analyses are disclosed, for example, in U.S. Pat. No. 8,315,812, filed Jan. 25, 2011 and entitled "Method and System for Patient-Specific Modeling of Blood Flow," which is hereby incorporated herein by reference in its entirety.

In one embodiment, permanent storage 125 may include past analyzed data, past received health data, population data, etc. Analysis generator 123 may process data of the anonymized data storage 121 along with data of the permanent storage 125. For example, machine learning algorithms trained on data of the permanent storage 125 may be used to calculate characteristics or metrics of data from the anonymized data storage 121. In one embodiment, permanent storage 125 may include historic or population data from past data transmissions or analyses, while anonymized data storage 121 may include data newly transmitted from the first region to the second region for analysis. For example, anonymized data storage 121 may include data that has not yet been analyzed, while permanent storage 125 may include data that has been analyzed by analysis generator 123 at least once before.

In one embodiment, analysis generator 123 may output reports of analyzed data, e.g., in the form of PDF files. In one embodiment, reports may include interactive elements. For example, reports may include interactive three-dimensional model(s), where users may zoom in/zoom out on various portions or segments of the model(s), prompt simulations, request data comparisons, etc. Simulations may include simulations of a patient's blood flow, blood pressure, treatment, physiological state, etc. Data comparisons may include colored interfaces, longitudinal data reports, charts, graphs, infographics, animations, etc. Various exemplary interactive displays and reports are described, for example, in U.S. Pat. No. 8,315,812, filed Jan. 25, 2011 and entitled "Method and System for Patient-Specific Modeling of Blood Flow," which is hereby incorporated herein by reference in its entirety. Various other displays and reports are described, for example, in U.S. patent application Ser. No. 14/480,870, filed Sep. 9, 2014, and entitled "Systems and Methods for Reporting Blood Flow Characteristics," which is hereby incorporated herein by reference in its entirety.

In one embodiment, analyzed data may be transmitted from the second region (e.g., cloud platform 120) to a first region (e.g., cloud platform 113). Alternatively or in addition, analyzed data may be retrieved by the first region from the second region. In one embodiment, analyzed data may be coupled to patient privacy information upon reentering the first region. For example, results store 119 of first region cloud platform 113 may receive analyzed data (e.g., where the analyzed data comprises PDF files). Identifiers related to each PDF may be matched to stored patient privacy information. For instances where patient privacy information includes PHI, hashes or identifiers associated with each PDF may be matched to PHI stored, for example, in the PHI storage 117. This way, analyzed data may be associated with its PHI once it is in the first region cloud platform 113. Patients, consumers, and/or medical professionals may access analyzed data once it is associated with the PHI. For example, a medical professional may retrieve analyzed data for a particular patient by interfacing with the results store 119 via consumer device(s) 130.

In one scenario, first region cloud platform 113 or its processor 115 may receive a request from a consumer device 130 to access analyzed data for a particular patient. The cloud platform 113 may determine if any reports of analyzed data of the results store 119 match any identifiers of the PHI database 117. If a match between a report and an identifier is detected, reports for the patient may be available. The cloud platform 113 may then prompt or permit consumer device(s) 130 to access the report of the results store 119 that corresponds to the particular patient's PHI. If no reports of the results store 119 correspond to the particular patient's PHI, the report may not yet be ready and the health data may still be undergoing analysis at the second region. In one embodiment, processor 115 may cause a prompt or notification to be sent or displayed to a consumer device 130 when a report for the patient is available.

By extension, in one embodiment, if a third region (distinct from both the first region and the second region) attempts to access the analyzed the data, the analyzed data may be available to the third region, albeit without associated patient privacy information. For example, an embodiment may include three regions, e.g., Europe, the United States (US), and Japan. Europe may serve as the first region where patient health data (including image data) is collected. All patient privacy information associated with the patient health data may remain in Europe, while collected image data is transmitted to the US for analysis. An analysis of the image data may be generated in the US and transmitted back to Europe. A physician may log into a portal and access the analyzed data for his/her patient in Europe. However, if the physician (or a partnering health care professional) in Japan visits the portal, the portal may show that analyzed data is available, without revealing patient privacy information associated with the data. In one instance, the analyzed data may be accessible or viewable in Japan, but without any identifying information for the patient associated with the analyzed data. The patient privacy information may be exclusive to data access in Europe, since the patient privacy information may not be transferred outside the border of the first region (e.g., Europe, in this example).

Similarly, a physician may collect data at a first hospital (either inside or outside the US). The data may be transmitted to a second region (e.g., the US) for analysis and analyzed data may be transmitted back to the first hospital. While at another hospital (e.g., the third region), the physician may see that analyzed data is available (and may even be able to interact with the analyzed data), while not being able to view the patient identity/patient privacy information associated with the analyzed data.

FIG. 2 is a flow diagram of an exemplary method 200 of transmitting health data via cloud platforms of different regions, according to an exemplary embodiment of the present disclosure. In one embodiment of method 200, health data may be collected at one region. For example, a cloud platform at a first region may receive collected health data (step 201). In one embodiment, step 201 may include receiving DICOM data or DICOM files, or accessing a DICOM database/library from the first region. Such collected health data may be associated with patient privacy information. For exemplary method 200, patient privacy information may include PHI.

In one embodiment, step 203 may include anonymizing the collected health data. For example, a cloud platform of the first region may strip the received health data of PHI. In one embodiment, step 203 may further include storing the PHI stripped from a received health data set, e.g., in a PHI database of the first region. In one embodiment, the PHI database may be included in a cloud platform, a local network, or any system of the first region. For example, step 203 may include identifying PHI fields based on regulatory requirements of the first region. For instance, in a DICOM file, step 203 may include detecting the Patient Name field (e.g., Tag (0010,0010), identifying the patient name, storing the patient name (e.g., in a database), and redacting the name from the DICOM with a generic (e.g., not nominative) string.

In one embodiment, step 205 may include creating one or more hashes of the PHI. Adding a hash may include computing and/or storing a hash (e.g., at a permanent storage). The hashes may be irreversible and created so they do not contain PHI. Accordingly, while the PHI may be retained in the first region, the hashes may be transferred to the second region along with the data (now decoupled from PHI). In other words, method 200 may entail ensuring that PHI associated with the health data may remain in the first region, while the health data (absent PHI) and the hash may be transmitted to the second region. Accordingly, step 207 may include transmitting anonymized health data to a second region. For example, transmitted health data may be associated with one or more hashes or other identifiers, while PHI remains exclusively within the first region (e.g., in the PHI storage).

In one embodiment, step 209 may include the anonymized health data being received at a second region. For example, an anonymized database of the second region may receive anonymized health data from the first region, where the anonymized health data is decoupled from PHI. The second region's anonymized database may store anonymized health data according to identifiers and/or hashes, since data transferred to the second region is no longer coupled to PHI. The anonymized database may store data of several forms, including DICOM storage, PDF storage (e.g., including PDF reports of analyzed data), or various auxiliary elements. In one embodiment, a portion or all of the received data may also be stored in a permanent storage at the second region, e.g., for record-keeping or for future analysis (step 211). Permanent storage may include a database.

In one embodiment, health data collected at the first region may be analyzed at the second region. For example, steps 213 and 215 may include analyzing anonymized health data received from the first region and generating a report based on analyzed data. In one embodiment, reports may include anonymized PDF files including analyzed data. For example, if data received from the first region includes raw image files, anonymized PDF files generated at the second region may include PDFs reporting blood flow characteristics determined based on an analysis of the raw image files. In such a case, the analysis may include generating anatomic models based on the received image files, calculating blood flow through the anatomic models, and deriving various metrics, displays, or predictions based on the calculated blood flow. In one embodiment, steps 213 and 215 may occur after step 211. For example, in some circumstances, permanent storage may include analyzed data and/or raw patient health data.

In one embodiment, step 217 may include transmitting analyzed data to the first region and step 219 may include matching analyzed data to a patient. For example, step 219 may include matching identifier(s) and/or hash(es) associated with the analyzed data, to identifier(s) and/or hash(es) associated with PHI stored in the PHI database of the first region.

Step 221 may include providing analyzed data to a consumer, e.g., a patient, a health care provider, a health care professional, etc. In one embodiment, step 221 may include informing a party of a completed report, for instance, via a notification at a web portal. For instance, step 221 may include generating an update at a portal interface and/or sending a notification to a user or user account.

FIGS. 3A-3D depict general embodiments of systems and methods, for instance, at a data collection and privacy preservation region. FIGS. 4A-4C depict general embodiments of systems and methods, for instance, at a data analysis region. It is understood that exemplary embodiments of FIGS. 3A-3D distinguish data collection/privacy preservation regions from data analysis regions of FIGS. 4A-4C for clarity. In practice, any geographic region may offshore its health data for analysis and/or analyze health data from other regions. In other words, any region may serve as a data collection/privacy preservation region for some transactions while serving as a data analysis region for other transactions.

Figure 3A:
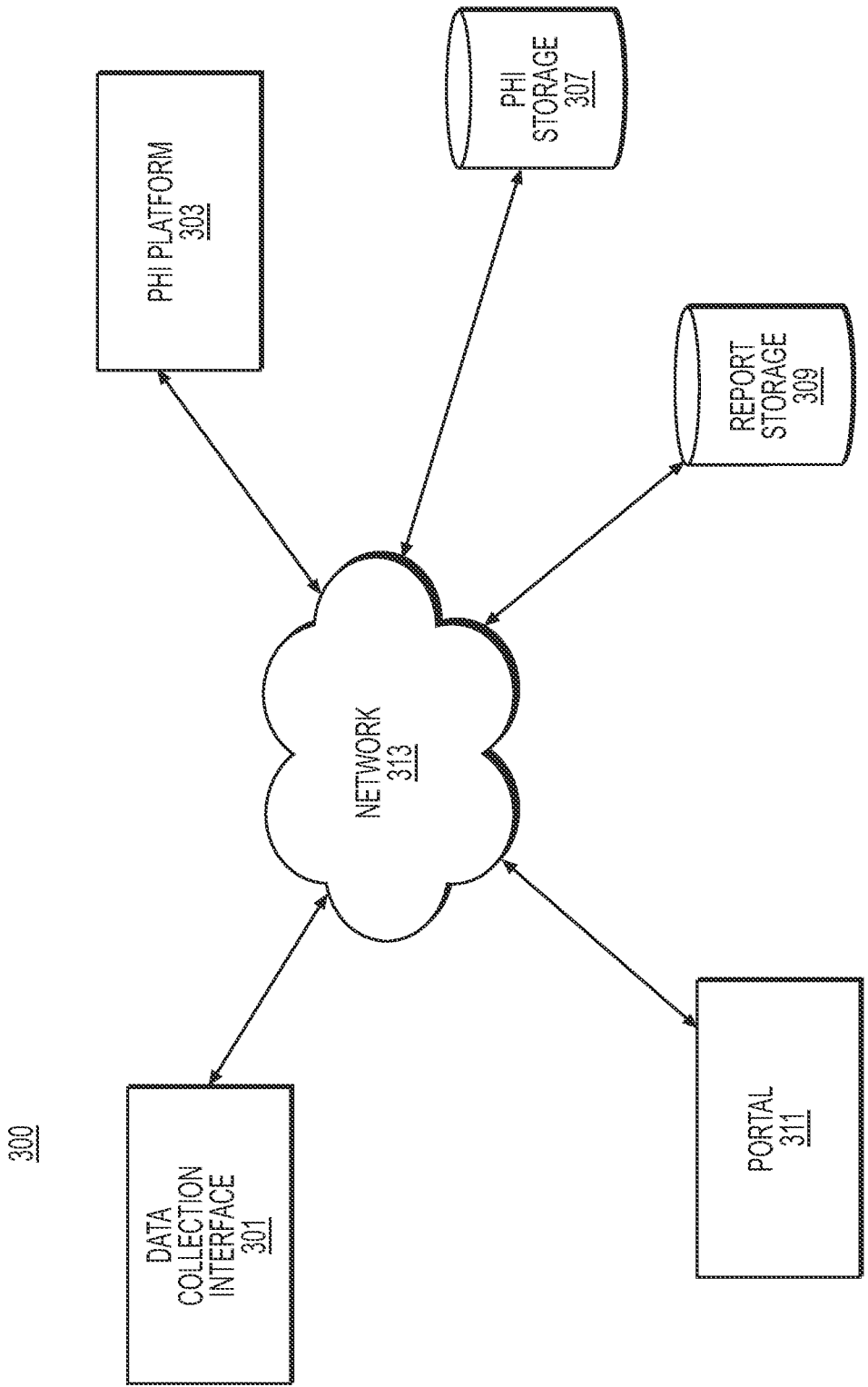
FIG. 3A is a block diagram of an exemplary data privacy system for transferring health data across a border without compromising patient privacy, according to an exemplary embodiment of the present disclosure.
Figure 3B:
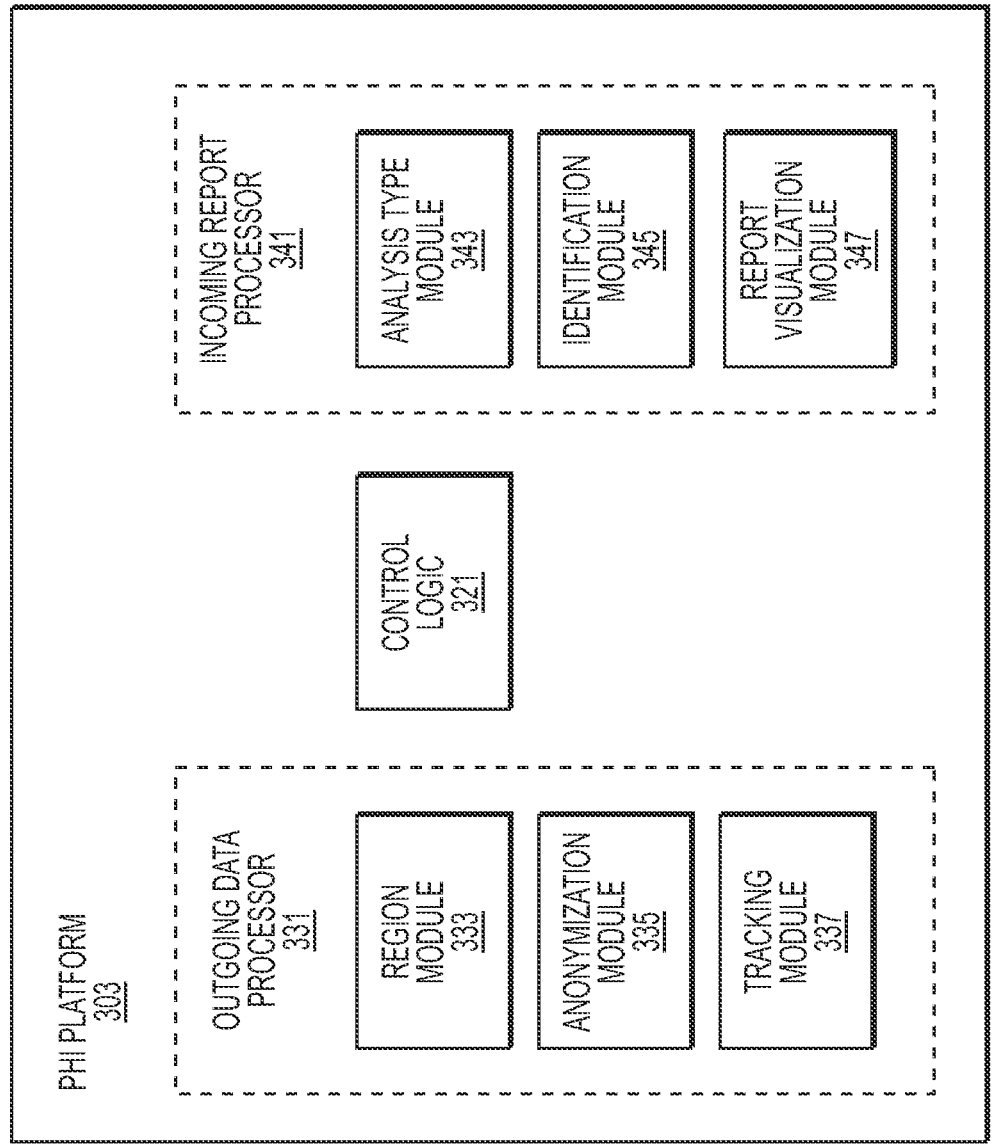
FIG. 3B block diagram of an exemplary patient privacy platform that may both prepare data for transfer to a second region and receive analyzed data from foreign region(s), according to an exemplary embodiment of the present disclosure.
Figure 3C:
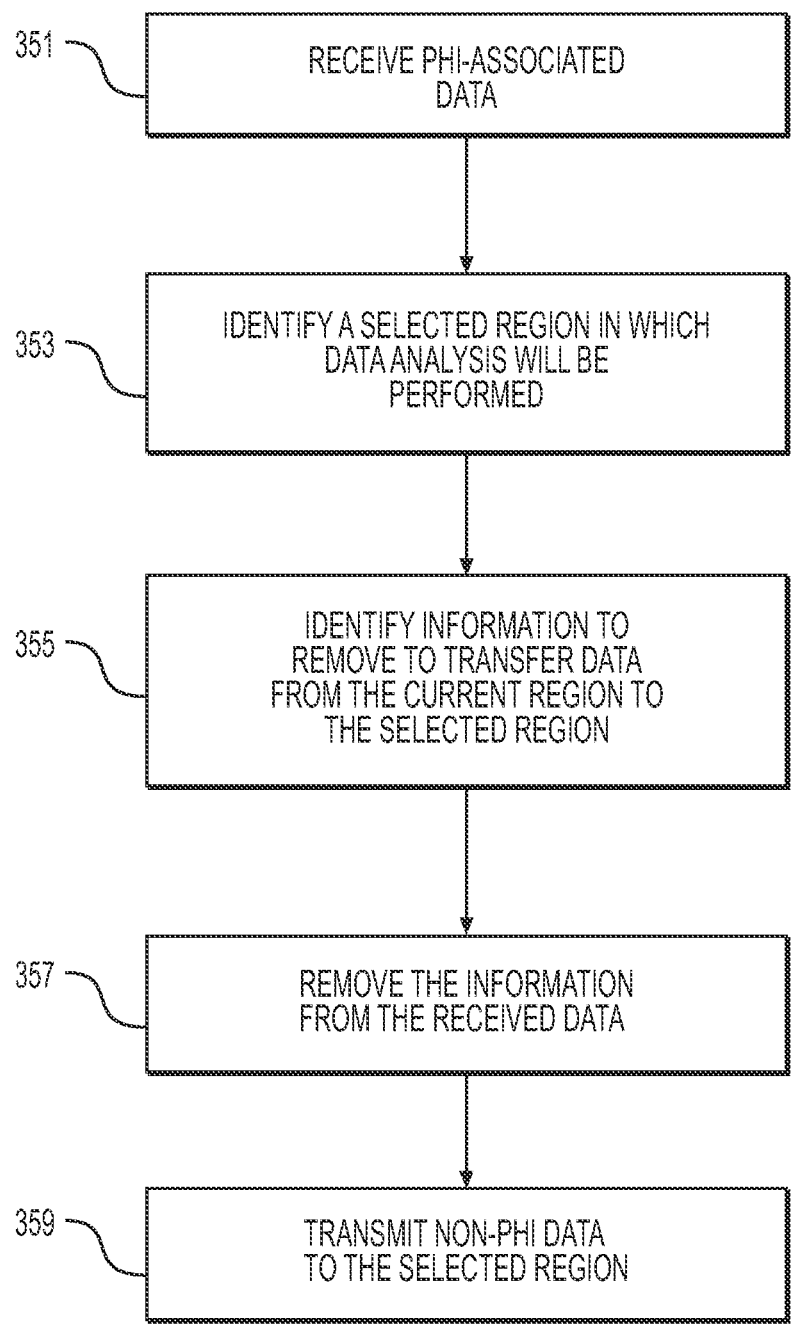
FIG. 3C is a flow diagram of an exemplary method of removing patient privacy information from health data, according to an exemplary embodiment of the present disclosure.
Figure 3D:
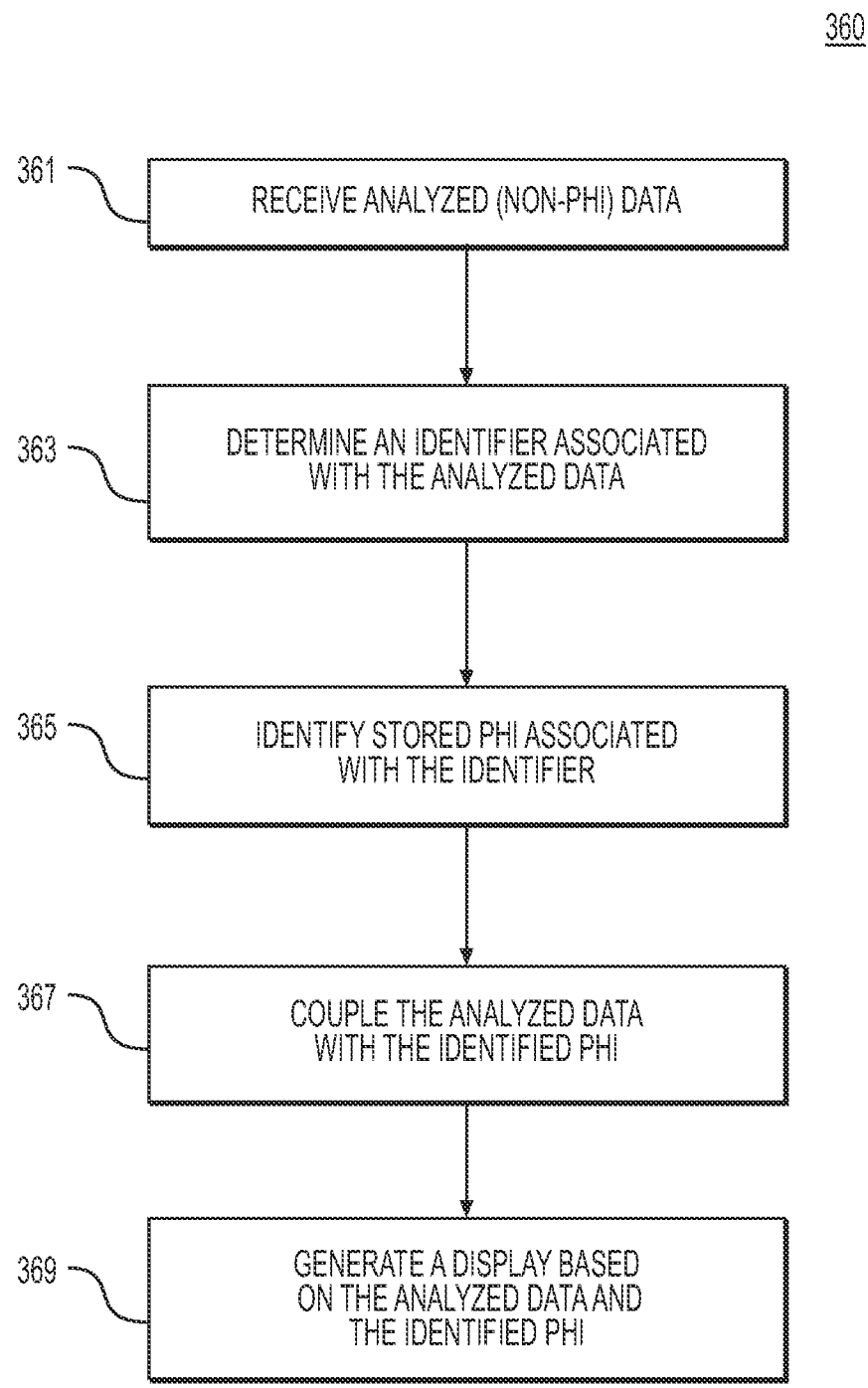
FIG. 3D is a flow diagram of an exemplary method of coupling analyzed data to stored patient privacy information, according to an exemplary embodiment of the present disclosure.
Figure 4A:
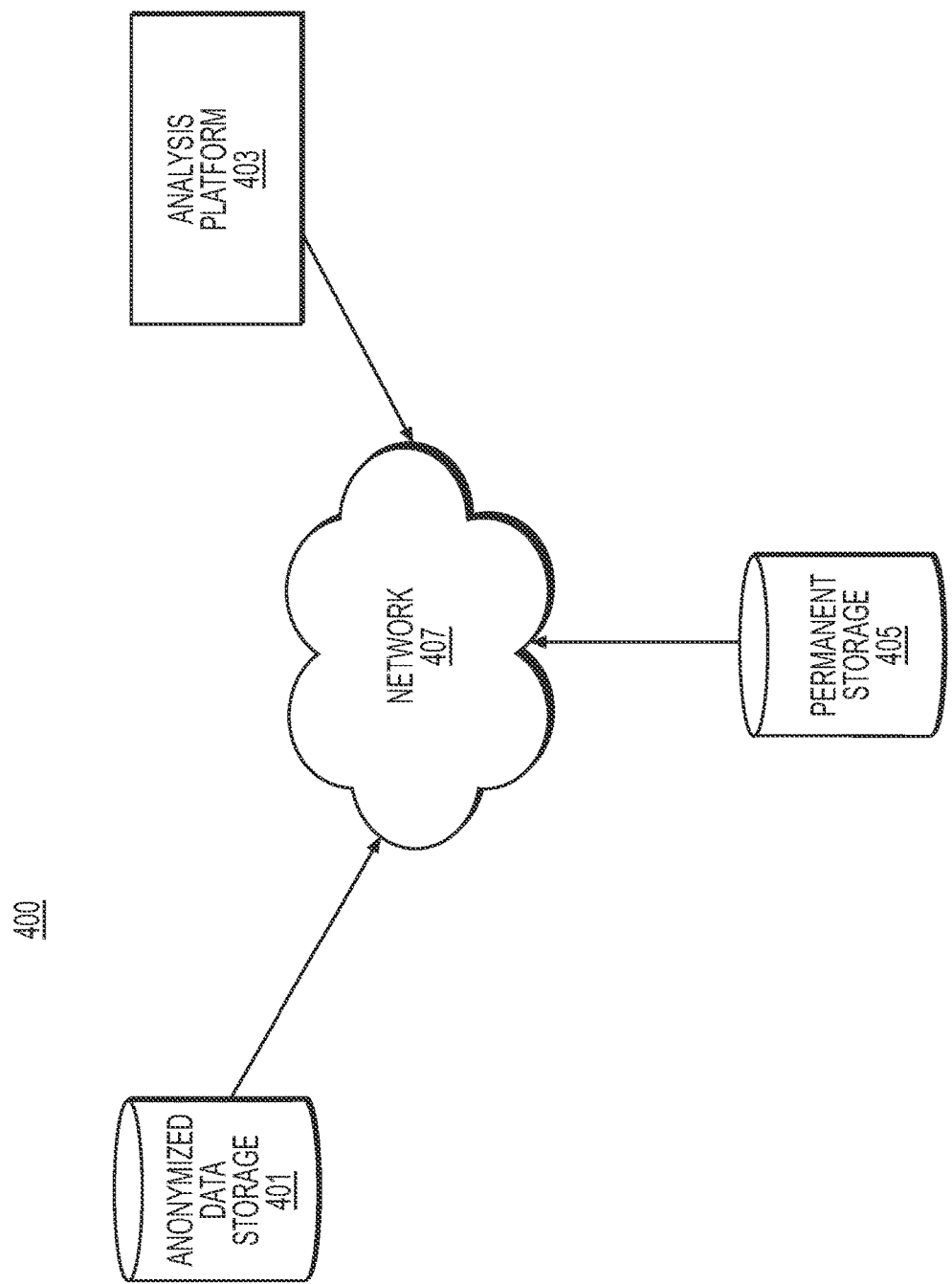
FIG. 4A is a block diagram of an exemplary data analysis system for analyzing anonymized data, according to an exemplary embodiment of the present disclosure.
Figure 4B:
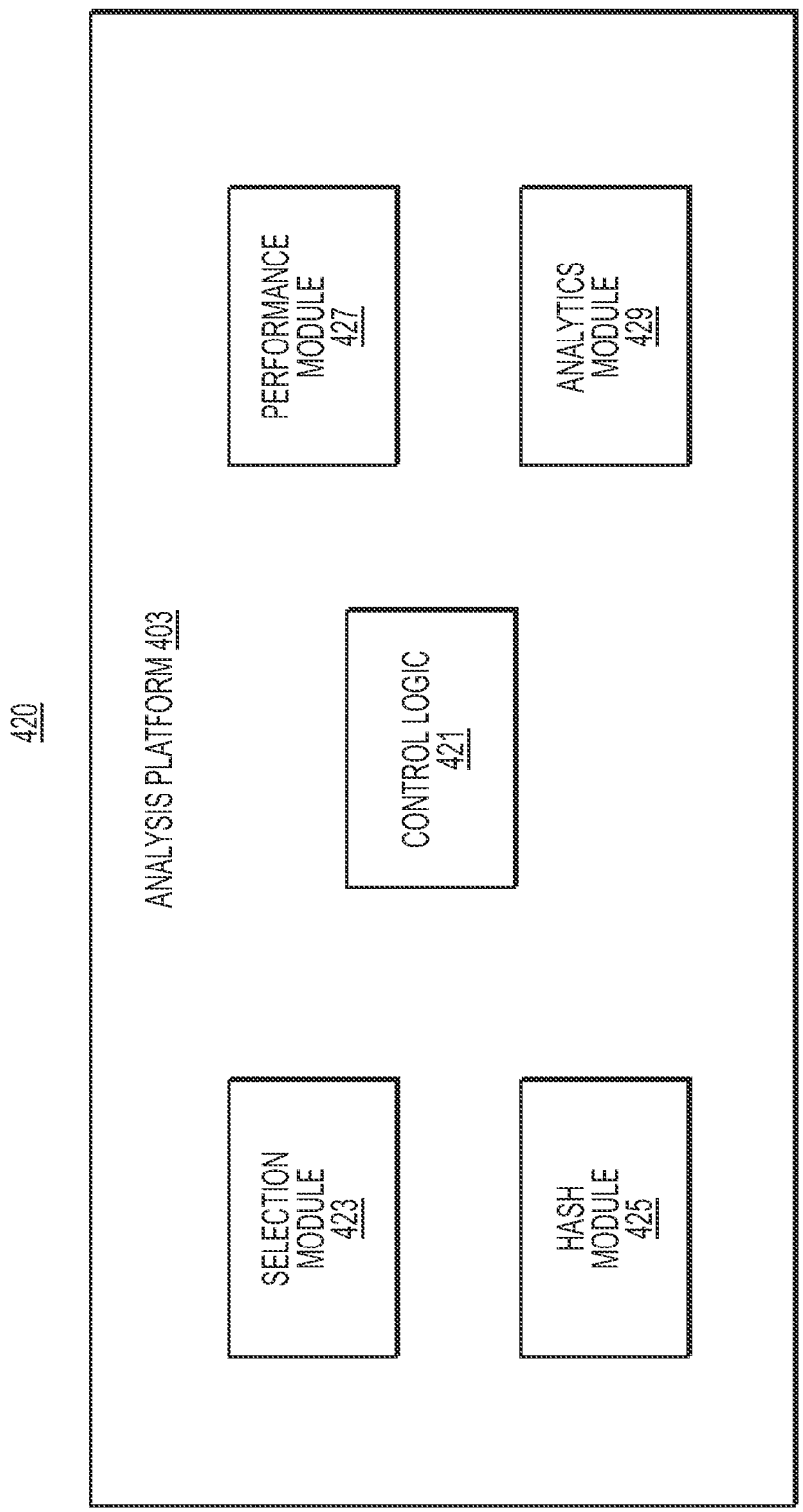
FIG. 4B block diagram of an exemplary analysis platform for analyzing health data received from a different region, according to an exemplary embodiment of the present disclosure.
Figure 4C:
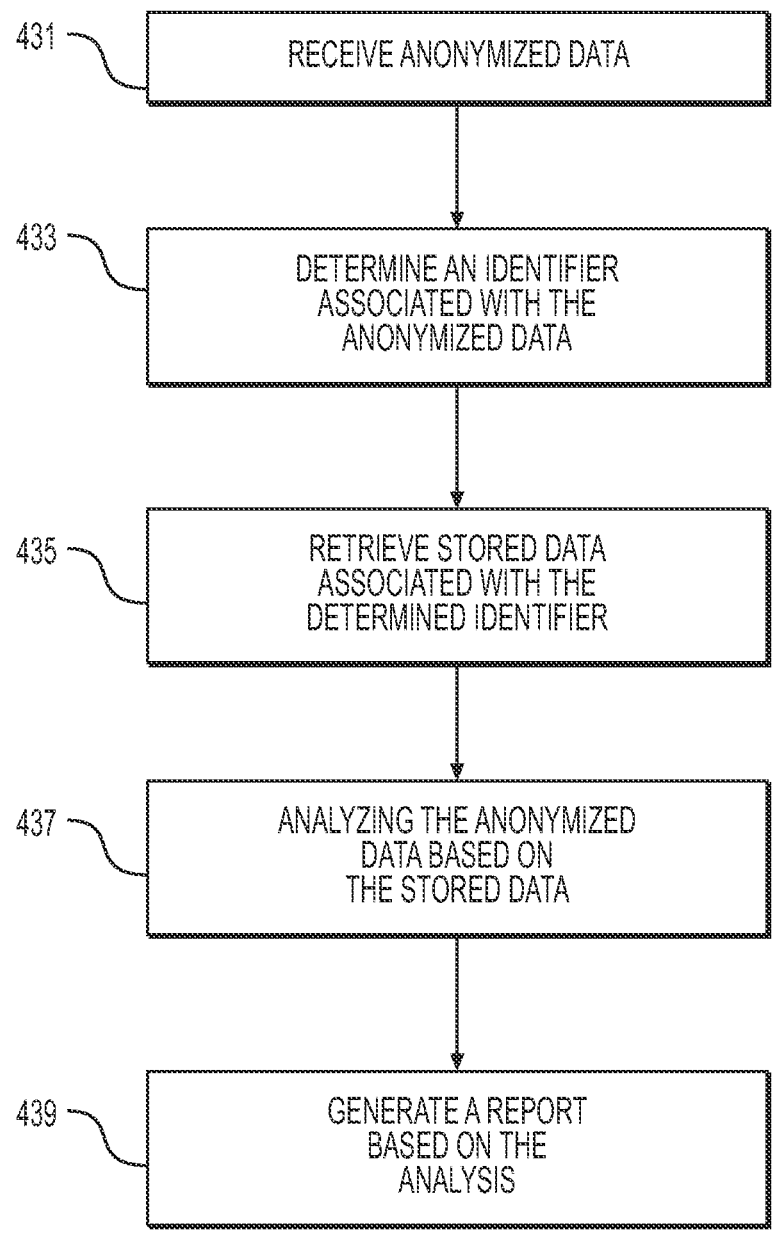
FIG. 4C is a flow diagram of an exemplary method of analyzing anonymized data, according to an exemplary embodiment of the present disclosure.

FIG. 3A depicts a system of exemplary cloud platform 113 at a first region where raw data may be generated. FIG. 3B depicts a schematic diagram of exemplary functions of a patient privacy information processor of the system (analogous to processor 115). FIG. 3C includes an exemplary process of removing patient privacy information from data prior to transmission of health data to a second region. FIG. 3D describes an exemplary process of coupling patient privacy information to analyzed data that is received from the second region. FIGS. 3A-3D depict patient privacy information as PHI, but it is understood that patient privacy information may include any protected personal information.

FIG. 3A depicts a block diagram of an exemplary data privacy system 300 for transferring health data across a border without compromising patient privacy, according to an exemplary embodiment. All components of the data privacy system 300 may exist in one region (e.g., Europe or Japan). Data privacy system 300 may be seen as a data offshoring system, in which data collected in the first region is prepared for transfer to a second (e.g., offshore region). Data may be analyzed in the second region. In addition, data privacy system 300 may process inbound analyzed data. For example, data privacy system 300 may receive analyzed data from a second region, e.g., in the form of completed reports. The analyzed data may be anonymized. Data privacy system 300 may couple analyzed data to patient privacy information so the reports may be accessed by patients and/or medical professionals on behalf of the patients. In one embodiment, data privacy system 300 may be comprised of various components including a data collection interface 301, a PHI platform 303, a PHI storage 307, a report storage 309, a portal 311, and a network 313. While exemplary system 300 describes patient privacy information as PHI (e.g., by way of the PHI platform 303 and PHI storage 307), it is understood that patient privacy information may include any information for securing patient privacy.

In one embodiment, data collection interface 301 may receive data collected and/or created in a first region. The PHI platform 303 may perform all the steps of preparing data for offshoring, as well as identifying associations between patient data and analyzed data. An exemplary PHI platform 303 is described in more detail FIG. 3B. In one embodiment, PHI storage 307 may store PHI decoupled from health data. In one embodiment, analyzed data returning from the second region may be coupled to associated PHI stored in the PHI database.

In one embodiment report storage 309 may receive and store analyzed data, e.g., in the form of PDF reports. Report storage 309 may be analogous to the results store 119 of FIG. 1. In one embodiment, users may access reports stored in report storage 309 via portal 311. In one embodiment, portal 311 may generate one or more user interfaces for patients/medical professionals to view reports of report storage 309. The user interfaces may include one or more interactive displays, including colored visual indicators, graphics, charts, tables, comparisons to previous patient reports or population data, treatment recommendations, etc. In one embodiment, portal 311 may generate or receive notifications when a patient's reports are available. For example, portal 311 may display a visual indicator on a user interface, showing that a patient report has been received in the first region. Portal 311 may also prompt a notification (e.g., a message received at a patient or medical professional's user device) when a report is available for access. Alternately or in addition, portal 311 may display visual indicators corresponding to the progress of an analysis or tracking the analyzed data. For example, portal 311 may display a user interface indicating, "report to be available in 3 days" or "please check back at 3 pm on Friday."

In one embodiment, various components of the data privacy system 300 (e.g., the PHI platform 303, report storage 309, and/or portal 311) may further analyze a patient's reports. For example, the data privacy system 300 may determine one or more recommended treatment regimens, therapy tasks, reports, follow-up tests/analyses, etc., and/or provide the recommended treatment regimens, therapy tasks, reports, follow-up tests/analyses, etc. via the portal 311. Alternately, all data/report analysis may be performed at the second region and the data privacy system 300 may exclusively identify which patient is associated with a set of analyzed data, and display the analyzed data to appropriate parties associated with the patient.

Network 313 may include the Internet, a content distribution network, or any other wired, wireless, and/or telephonic or local network. Data collection interface 301, PHI platform 303, PHI storage 307, report storage 309, portal 311, and various user and/or administrator devices may communicate with each other via network 313.

In one embodiment, users may access the data collection interface 301 and/or portal 311 via network 313 and one or more devices. Devices may include any type of electronic device configured to collect, send, and/or receive data, such as websites and multimedia content, over network 313. Devices may include medical devices, e.g., medical imaging devices, medical monitors, etc. Devices may also include one or more mobile devices, smartphones, personal digital assistants ("PDA"), tablet computers or any other kind of touchscreen-enabled device, a personal computer, a laptop, and/or server disposed in communication with network 313. Each of the devices may have a web browser and/or mobile browser installed for receiving and displaying electronic content received from one or more of web servers affiliated with data privacy system 100. The devices may include client devices that may have an operating system configured to execute a web or mobile browser, and any type of application, e.g., a mobile application. In one embodiment, various devices may be configured with network adapters to communicate data or analyzed reports over network 313. Alternatively, or additionally, various may be configured to transmit data or receive analyzed data over a local connection.

FIG. 3B is a block diagram 320 of PHI platform 303 for preparing data for transfer to a second region and receiving analyzed data from foreign region(s), according to an exemplary embodiment of the present disclosure. As shown in FIG. 3B, exemplary PHI platform 303 may include a control logic 321. Control logic 321 may direct the functions and interactions among the various modules and processors that may be operating as part of PHI platform 303. PHI platform 303 may manage outgoing data for offshore data analysis, for instance, by removing PHI data from a dataset (e.g., via outgoing data processor 331). PHI platform 303 may further manage data analyzed offshore, as it re-enters a region, for instance, by coupling data to appropriate PHI (e.g., via information report processor 341). The outgoing data processor 331 and the information report processor 341 will be discussed in detail below.

In one embodiment, the control logic 321 and outgoing data processor 331 may prepare collected data for transmission to a second region. For example, PHI platform 303 may be in a first region, and PHI platform 303 may process data leaving the first region to enter a second region. Legal restrictions may exist when transmitting information that is linked to a patient's identity. Various legal regimes or systems may follow different restrictions. Thus, in order to transfer PHI-associated health data to another region, the health data may be decoupled or disassociated with the patient and corresponding PHI.

In one embodiment, such data may be processed by outgoing data processor 331, comprising exemplary modules, e.g., region module 333, anonymization module 335, and tracking module 337. In one case, outgoing data processor 331 may remove protected health information or patient privacy information from health data collected in the first region. Removing the protected health information or patient privacy data may remove associations between a patient's identity and data collected from the patient.

In one embodiment, region module 333 and control logic 321 may identify which region data is being transferred to (e.g., a second region). Region module 333 and control logic 321 may determine any privacy regulations involved in transferring the data from the first region to the second region.

In one embodiment, anonymization module 335 and control logic 321 may perform the steps needed to meet privacy regulations. For example, anonymization module 335 and control logic 321 may remove and/or manipulate PHI elements of received datasets to permit the transfer of the datasets.

In one embodiment, tracking module 337 and control logic 321 may track or transmit data to the designated or previously identified second region. For example, tracking module 337 and control logic 321 may provide a way to track data decoupled from PHI. For example, tracking module 337 and control logic 321 may create hashes of PHI elements. Such hashes may provide the ability to longitudinally track data at different time points. For example, PHI platform 303 may receive a first scan (e.g., from data collection interface 301. The first scan may be associated with a patient, "John Doe." The anonymization module 335, tracking module 337, and/or control logic 321 may store hashes for "John" and "Doe." Exemplary hashes may be absent of PHI and/or be irreversible. In one embodiment, data may be transferred to the second region with hashes to track or identify the data set, while PHI data remains within the first region. Processors at the second region may then use hashes to track or determine that various sets of data are related to each other.

Various hash functions may be used, including, for example, SHA1, MD5, bcrypt, etc. Information fields that may be hashed include: patient's first name, patient's last name, patient ID, patient's data of birth, referring physician's first name, referring physician's last name, date of data creation, time of data creation, etc.

PHI platform 303 may further manage data analyzed offshore, as it re-enters a region. For instance, PHI platform 303 may couple analyzed data to corresponding PHI. In one embodiment, incoming report processor 341 may receive completed analyses of data (e.g., in the form of reports). In one embodiment, reports may be created based on metadata and/or models (e.g., three-dimensional anatomic models) associated with PHI corresponding to the analyzed data. Incoming report processor 341 may identify patients associated with the reports and pair the reports with patients or PHI/identification information. In one embodiment, the incoming report processor 341 may include exemplary modules, e.g., analysis type module 343, identification module 345, and report visualization module 347.

In one embodiment, analysis type module 343 and control logic 321 may receive data, e.g., from a second region. In one embodiment, analysis type module 343 and control logic 321 may sort or organize received data, e.g., from report storage 309. For instance, received data may include data that has undergone a form of analysis. For example, received data may arrive in the form of a portable document format (PDF) file comprising a report. Sorting or organizing received data may include recognizing received data in terms of the timing that it was received, the region from which it was received, the medium in which the data is received, etc.

In one embodiment, identification module 345 and control logic 321 may couple PHI to the received data or report. For example, identification module 345 and control logic 321 may access PHI storage 307 and match the received data (e.g., from the report storage 309) to respective PHI from the PHI database 107.

In one embodiment, the control logic 321, analysis type module 343, and/or the identification module 345 may receive a plurality of received analyses (e.g., a plurality of reports from the report storage 309). The plurality of reports may be processed by the analysis type module 343, identification module 345, and/or control logic 321 to determine associations between the reports or previously stored reports (e.g., reports from an earlier time). Temporal linking of analyzed data may take place via the use of hashes. For example, the incoming report processor 341 may receive a hash associated with analyzed data and establish a longitudinal view of a patient's medical condition based on the received hash.

In one embodiment, report visualization module 347 and control logic 321 may govern the display or availability of analyzed data to parties wishing to view the analyzed data. In one embodiment, report visualization module 347 may include direct access to PDF reports, models associated with or included in the reports, etc. The analyzed data may be displayed with overlaid PHI information corresponding to the analyzed data. The various forms of analyzed data may be available via one or more platforms e.g., a web portal, mobile device, virtual reality display, television screen, laptop computer, desktop computer, etc.

FIG. 3C is a flow diagram of an exemplary method 350 of removing patient privacy information from health data, according to an exemplary embodiment. The method of FIG. 3C may be performed by outgoing data processor 331 and control logic 321, based on information, images, and data received from data collection interface 301 over electronic network 313. Method 350 may be performed using a processor (e.g., laptop, desktop, cloud computing architecture, graphics processing unit (GPU), digital signal processor (DSP), mobile phone, tablet, etc.).

In one embodiment, step 351 may include receiving health data associated with PHI (e.g., at a first region). The health data may be received from medical professionals, imaging devices, and/or third party medical service providers, e.g., via data collection interface 301.

In one embodiment, step 353 may include identifying a selected region in which data analysis will be performed. For example, health data may be received at a first region (e.g., the United States). Step 353 may include determining that the received health data is to be transferred to Europe for data analysis. Step 353 may also include receiving various requests for analyses to be performed on the received health data and determining which region(s) to which the health data may be transferred.

In one embodiment, step 355 may include identifying information to remove in order to transfer health data (from the first region) to the selected region. For example, restrictions currently exist against transferring PHI out of the United States. In one embodiment, step 357 may include removing the patient privacy information from the received health data. For instance, if health data is to be transferred out of the United States, step 355 may include identifying PHI to remove from collected health data, as well as removing the identified PHI from the collected health data. For example, step 355 may include identifying PHI fields that are considered patient privacy information for all the regions that interact with the first region. As another option, step 355 may include removing all PHI fields not used for case processing. Yet another embodiment may include removing PHI fields specifically for the first region, or depending on the relationship between the first region and the second region. An exemplary instance may include a first region being a hospital clinic and a second region being a hospital lab. For such a case, there could be PHI fields that do not have to be removed for the transmission of the health data between the first region and second region, which may have to be removed to transfer the health data out of the hospital.

In one embodiment, step 359 may include transmitting anonymized health data to the selected region, where the transmitted health data does not include patient privacy information (e.g., PHI). In one embodiment, step 359 may further include tagging the transmitted data with an identifier unrelated to the patient privacy information. The identifier may be random, not data-specific, and/or associated with a region, time/date, hospital, etc. In one embodiment, the identifier may be used to track the health data in the absence of patient privacy information.

Furthermore, step 359 may include hashing patient privacy information. For example, the data may be transmitted to the selected region with hashes of the patient privacy information, while the patient privacy information remains exclusively in the first region.

The steps of FIG. 3C may be performed in a variety of orders. While the exemplary embodiment includes identifying a selected region (step 353), identifying information to remove (step 355), and removing the identified information (step 357), there are many alternatives. For example, an alternative embodiment may include receiving patient health data (step 351), removing all patient privacy information associated with the patient health data, and then transferring the patient health data to any region. For example, method 300 may include identifying, for the first region, all patient privacy information fields to redact in order to transfer the health data to any region. In another example, the first region may automatically remove a subset of PHI, sufficient to permit sending of the data out of the first region. For these scenarios, the removal of PHI data may not be affected by the region in which data analysis would be performed. Method 300 may include identifying a configuration, per region, of patient privacy information fields to redact. The configuration may be stored in any storage, e.g., a database.

FIG. 3D is a flow diagram of an exemplary method 360 of coupling analyzed data to stored patient privacy information, according to an exemplary embodiment. The method of FIG. 3D may be performed by incoming report processor 341 and control logic 321, based on information, images, and data received from the second region. Method 360 may be performed using a processor (e.g., laptop, desktop, cloud computing architecture, graphics processing unit (GPU), digital signal processor (DSP), mobile phone, tablet, etc.).

In one embodiment, step 361 may include receiving analyzed data, e.g., in the form of PDF reports. The analyzed data may be anonymized and not associated with any patient privacy information (e.g., PHI). In one embodiment, step 361 may include receiving, at a first region, analyzed data from a selected/second region.

In one embodiment, step 363 may include determining or receiving an identifier associated with the analyzed data. For example, the identifier may be the identifier that a patient data set was tagged with (e.g., at method 350). Alternately, the identifier may be an identifier associated with an identifier created at the first region. The identifier may include a unique global ID that may be shared across regions. For example, the identifier may include a date (MM/DD/YY) sequence and a unique number and/or letter combination.

In one embodiment, step 365 may include identifying stored patient privacy information associated with the determined/received identifier. Step 367 may include coupling the analyzed data with the identified patient privacy information. In one embodiment, steps 365 and 367 may include generating artifacts that an end-user may use with corresponding PHI information. For example, step 367 may include regenerating reports of analyzed data that include PHI information that remained in the region. For instance, PHI information may be retrieved from an API at the first region and a reporting tool (e.g., report visualization module 347) may insert the PHI information in generated reports. This type of mechanism may be extended to any file or medium used by an end-user to interact with analyzed data, including PDFs encapsulated in DICOM files, graphical user interfaces, holograms, etc.

In one embodiment, step 369 generating one or more displays based on the analyzed data and identified patient privacy information. Exemplary displays for end-users may include PDF reports accessible through a portal, two-dimensional and/or three-dimensional models with PHI information available through a portal, push of reports through a hospital infrastructure for visualization on hospital systems, etc.

FIGS. 4A-4C depict exemplary systems and methods of a data analysis region. FIG. 4A depicts a system of exemplary cloud platform 120 at a second region where anonymized health data may be analyzed. FIG. 4B depicts a schematic diagram of exemplary functions of a data analysis platform of the system (analogous to analysis generator 123). FIG. 4C depicts an exemplary process of analyzing anonymized health data.

FIG. 4A depicts a block diagram of an exemplary data analysis system 400 for analyzing anonymized data, according to an exemplary embodiment. Data analysis system 400 may be comprised of various components including an anonymized data storage 401, an analysis platform 403, a permanent storage 405, and a network 407. In one embodiment, anonymized data storage 401 may receive and store data received from a region other than the region of the data analysis system 400. For example, anonymized data storage 401 may store health data decoupled from any patient or identification information. In one embodiment, anonymized data storage 401 may receive data associated with identifier(s) and/or hash(es) unrelated to patient privacy information. In another embodiment, anonymized data storage 401 may store or tag received data with identifier(s) and/or hash(es).

In one embodiment, analysis platform 403 may perform the same type of analysis for any data stored in the anonymized data storage 401. In another embodiment, the analysis platform 403 perform a different type of data analysis, depending on one or more factors, e.g., the type of data stored in anonymized data storage 401, the sender (e.g., processor 115), the region from which data is received, a subscription service, a hospital/research facility/medical service provider/cloud service associated with the data, etc.

For example, performing data analysis based on data type may include a scenario where the analysis platform 403 may detect a certain type of health data file or differentiate between various types of data files. For instance, if anonymized data storage 401 includes a DICOM file, the analysis platform 403 may generate an anatomic model based on the DICOM file and perform a predetermined series of analyses (e.g., blood flow analyses) using the generated anatomic model. Alternately, if anonymized data storage 401 includes a file of blood pressures, the analysis platform 403 may perform a blood pressure analysis separate from the blood flow analyses associated with DICOM files. In some embodiments, the analyses may overlap, while in other embodiments, the analysis platform 403 may be configured to perform distinct sets of analyses depending on types of files received or stored by the anonymized data storage 401.

In embodiments where analysis may be related to a region, subscription, or facility from which the anonymized data is received, analysis platform 403 may determine data analysis requests associated with the sender of the anonymized data. For example, a hospital may subscribe to a service that may provide blood flow analyses for the hospital's patients. Upon detecting that anonymized data is related to this type of subscription service, analysis platform 403 may prompt performance of a blood flow analysis on the anonymized data. Similarly, analysis platform 403 may determine that all data from particular region, "Region X," is to undergo a certain type of analysis, "Analysis A." Accordingly, analysis platform 403 may perform Analysis A (or prompt performance of Analysis A) on any data received from Region X.

Alternately or in addition, analysis platform 403 may be configured to offer access to various types of data analysis. Data transmitted from the first region may include commands or indications as to the types of data analysis requested to be performed by analysis platform 403 in the second region. For example, a type of blood flow analysis may be unavailable in the first region, but available in the second region. The first region may transmit anonymized health data to the second region, along with the request for the particular type of blood flow analysis to be performed. The analysis platform 403 may receive the request for the type of blood flow analysis, perform the analysis, and prompt the transfer of the analyzed data to the first region where the analyzed data may be coupled to the corresponding patient.

In one embodiment, permanent storage 405 may comprise a repository of cases and data that may improve algorithms used for data analysis, e.g., including machine learning or deep learning. The more cases processed and/or available in permanent storage 405, the more accurate the data analysis may be. Permanent storage 405 may also be used for dashboarding of stored/known/past-analyzed data and/or analytics. Dashboarding may include various visualizations, metrics, and options for organizing data or formulating analyses. For example, dashboarding may sort data into categories (e.g., types of analysis, region, etc.), and offer selections on data sets to use for an analysis. Visualizations may include bar graphs, graphical icons, dials, emoticons, symbols, charts, graphs, etc. Analytics may include, for example, analytics that may refine data analysis based on regions, demographics, timings, etc. In one embodiment, permanent storage 405 may include permanent raw and/or analyzed data, as well as empirical data, population data, experimental data, etc. Permanent storage 405 may further store hashes.

Analysis platform 403 may access permanent storage 405 to enhance its analyses. For example, analysis platform 403 may employ machine learning mechanisms trained on data of permanent storage 405. Analysis platform 403 may analyze data from anonymized data storage 401, based on data of permanent storage 405. In one embodiment, analyzed data may be stored by permanent storage 405 for future analyses.

In another embodiment, data analysis system 400 may permit the comparison of stored hash(es) against hash(es) associated with received health data. For example, data analysis system 400 may store hashes for a first set of data received from the first region. At a later point in time, data analysis system 400 may receive a different set of data from the first region, where this second set of data is associated with a second set of hashes. Data analysis system 400 may compare the second set of hashes to hashes stored (e.g., by the anonymized data storage 401 and/or permanent storage 405), and determine if the first data set and the second data set may be related (e.g., associated with the same patient). If so, data analysis system 400 may analyze the second set of data while taking into account the first set of data. In this way, data analysis system 400 may permit longitudinal studies or studies of one or more patients over time.

Network 407 may include the Internet, a content distribution network, or any other wired, wireless, and/or telephonic or local network. Anonymized data storage 401, analysis platform 403, permanent storage 405, and various user and/or administrator devices may communicate with each other via network 407.

FIG. 4B is a block diagram of an exemplary model 420 of analysis platform 403 for analyzing health data received from a different region, according to an exemplary embodiment of the present disclosure. As shown in FIG. 4B, exemplary analysis platform 403 may include a control logic 421. Control logic 421 may direct the functions and interactions among the various modules and processors that may be operating as part of analysis platform 403. The other modules and processors may include a selection module 423, a hash module 425, a performance module 427, and an analytics module 429.

In one embodiment, the control logic 421 and selection module 423 may receive health data from the first region and determine which analysis to perform on the health data. For example, analysis platform 403 may include access to multiple different forms of analyses. Selection module 423 and control logic 421 may determine the appropriate analysis to perform for a given health data set, based on the region from which the health data is received, the hospital from which the data is received, a subscription service associated with the health data, etc.

In one embodiment, the control logic 421 and hash module 425 may determine a hash associated with the received health data and determine if the hash is associated with any stored hashes. For example, control logic 421 and hash module 425 may compare a hash associated with a newly received data set and determine whether any data of the anonymized database 401 and/or permanent storage 405 corresponds to the hash of the newly received data set. Correspondence between a newly received hash and a stored hash may indicate that the received health data is associated with the same patient. Alternately or in addition, correspondences between hashes may also indicate relationships between data sets other than the data sets being associated with the same patient. For example, correspondences between hashes may indicate that various data files/sets were all generated or sent by the same hospital or physician.

Correspondences between hashes may also indicate patients within a certain age range or demographic. In short, the control logic 421 and hash module 425 may determine relationships between data sets.

In a further embodiment, control logic 421 and hash module 425 may determine whether other data sets may be used for analysis of a received health data set. For example, control logic 421 and hash module 425 may determine that several data sets may be associated with the same patient (despite not knowing the identity of the patient). Control logic 421 and hash module 425 may then prompt data analysis based on a portion of the data associated with the same patient, possibly in addition to analysis of the received data set. Control logic 421 and hash module 425 may also determine that several data sets correspond to patients of a certain age range, although no data corresponds to the particular patient associated with a received data set. In one embodiment, control logic 421 and hash module 425 may prompt data analysis that takes into account other patient data from patients within a given age range, when analyzing the received data set.

In one embodiment, control logic 421 and performance module 427 may perform analysis on the received health data. For example, data analysis may be based on the analysis selected (e.g., determined by the control logic 421/selection module 423) and by data related to the received data (e.g., as determined by the control logic 421/hash module 425). In one embodiment, control logic 421 and performance module 427 may perform analyses of health data without using stored data. Alternately, control logic 421 and performance module 427 may access permanent storage 405 to perform and/or supplement analysis of received health data. In one embodiment, control logic 421 and performance module 427 may further generate reports of the completed analysis.

In one embodiment, control logic 421 and analytics module 429 may update and/or refine analysis techniques, based on the analyzed data. For example, control logic 421 and analytics module 429 may update analysis techniques for future data analysis.

FIG. 4C is a flow diagram of an exemplary method 430 of analyzing anonymized data, according to an exemplary embodiment. Method 430 may be performed using a processor (e.g., laptop, desktop, cloud computing architecture, graphics processing unit (GPU), digital signal processor (DSP), mobile phone, tablet, etc.) communicating over electronic network 417, e.g., at a cloud platform in a second region.

In one embodiment, step 431 may include receiving anonymized data, e.g., from a different region. Step 433 may include determining an identifier associated with the anonymized data. In one embodiment, step 435 may include identifying and/or retrieving stored, population, empirical, historical, and/or experimental data associated with the determined identifier. Step 437 may include performing analysis on the anonymized data, based on the identified/retrieved data associated with the identifier. In one embodiment, step 439 may include generating a report of the analyzed data, e.g., in the form of a PDF file. Step 439 may further include transmitting the analyzed data back to region from which the anonymized data was received (e.g., a first region). The analyzed data report may be anonymous when it is transmitted back to the first region.

The present disclosure includes a system and method for decoupling patient privacy data from health data prior to the health data being transmitted out of a first region to a second region. The present disclosure further includes a system and method for coupling analyzed data to a patient when the analyzed data returns from the second region to the first region. Accordingly, data analysis may be provided across regions, while avoiding the transfer of privacy data from one region to another.

Any of the described embodiments may be modified, for example, to include variations of data that may be kept within a region. The disclosed systems and methods may be modified to model and assess any range of changes to circulation.

Program aspects of the technology may be thought of as "products" or "articles of manufacture" typically in the form of executable code and/or associated data that is carried on or embodied in a type of machine readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of processing electronic images while transferring data across regions, the method comprising:

removing, using a processor physically located in a first region, first patient-identifiable information from patient-specific data to generate a first set of de-identified data, based on a first geographic region specific privacy standard;

storing, using the processor physically located in the first region, the first patient-identifiable information within the first region;

transmitting, using the processor physically located in the first region, the first set of de-identified data to a remote data analysis server physically located in a second region for a patient-specific computation based on the first set of de-identified data;

generating, using the remote data analysis server physically located within the second region, a model of a patient based on the first set of de-identified data and conducting the patient-specific computation through the generated model;

determining, using the remote data analysis server physically located within the second region, a patient-specific blood flow computation in the patient based on the generated model and a mass or a volume of a myocardial tissue of the patient;

receiving, by the processor physically located in the first region, analyzed de-identified data from the remote data analysis server physically located in the second region; and identifying a patient associated with the generated model by determining, using the processor physically located in the first region, first patient-identifiable information associated with the analyzed de-identified data based on the first patient-identifiable information stored within the first region and the patient-specific blood flow computation stored in a permanent storage at the second geographic region, wherein the first patient privacy information is inaccessible within the second geographic region.

2. The computer-implemented method of claim 1, wherein the second region is distinct from and outside the first region, and wherein the first region and the second region are governed by different data anonymization regulations.

3. The computer-implemented method of claim 1, further comprising:

generating, using the processor physically located in the first region, an identifier associated with the first set of de-identified data, wherein the first patient-identifiable information is absent from the identifier.

4. The computer-implemented method of claim 1, wherein the analyzed de-identified data includes results of a patient-specific blood flow computation calculated at an earlier date and stored in the permanent storage.

5. The computer-implemented method of claim 1, further comprising:

generating, using the processor physically located in the first region, an irreversible hash of the first patient-identifiable information.

6. The computer-implemented method of claim 1, further comprising:

prompting refining of modeling techniques available at the second region, based on the analyzed de-identified data.

7. The computer-implemented method of claim 1, further comprising:

determining, using the processor physically located in the first region, an identifier associated with the analyzed de-identified data from the second region;

determining, using the processor physically located in the first region, an association between the identifier and the first patient-identifiable information stored within the first region; and determining, using the processor physically located in the first region, the first patient-identifiable information corresponding to the analyzed de-identified data based on the association between the identifier and the first patient-identifiable information stored within the first region.

8. The computer-implemented method of claim 1, further comprising:

determining, using the processor physically located in the first region, a hash associated with the analyzed de-identified data or the first set of de-identified data; and determining, using the processor physically located in the second region, previously analyzed data associated with either the analyzed de-identified data or the first set of de-identified data, based on a comparison of the hash to one or more stored hashes.

9. A system for processing electronic images while transferring data across regions, the system comprising:

at least one data storage device physically located within a first region and storing instructions for providing cross-border data transfer while preserving first data anonymization; and at least one processor physically located within the first region and configured to execute the instructions to perform operations comprising:

removing, using a processor physically located in a first region, first patient-identifiable information from patient-specific data to generate a first set of de-identified data, based on a first geographic region specific privacy standard;

storing, using the processor physically located in the first region, the first patient-identifiable information within the first region;

transmitting, using the processor physically located in the first region, the first set of de-identified data to a remote data analysis server physically located in a second region for a patient-specific computation based on the first set of de-identified data;

generating, using the remote data analysis server physically located within the second region, a model of a patient based on the first set of de-identified data and conducting the patient-specific computation through the generated model;

determining, using the remote data analysis server physically located within the second region, a patient-specific blood flow computation in the patient based on the generated model and a mass or a volume of a myocardial tissue of the patient;

receiving, by the processor physically located in the first region, analyzed de-identified data from the remote data analysis server physically located in the second region; and identifying a patient associated with the generated model by determining, using the processor physically located in the first region, first patient-identifiable information associated with the analyzed de-identified data based on the first patient-identifiable information stored within the first region and the patient-specific blood flow computation stored in a permanent storage at the second geographic region, wherein the first patient privacy information is inaccessible within the second geographic region.

10. The system of claim 9, wherein the second region is distinct from and outside the first region, and wherein the first region and the second region are governed by different data anonymization regulations.

11. The system of claim 9, wherein the operations at the remote data analysis server physically located within the first region further comprise:

generating an identifier associated with the first set of de-identified data, wherein the first patient-identifiable information is absent from the identifier.

12. The system of claim 9, further comprising:

transmitting the first set of de-identified data to the second region with the generated identifier.

13. The system of claim 9, wherein the operations at the remote data analysis server physically located within the first region further comprise:

generating an irreversible hash of the first patient-identifiable information.

14. The system of claim 9, the operations further comprising:
prompting refining of blood flow modeling techniques available at the second region, based on the analyzed de-identified data.

15. The system of claim 14, wherein the operations at the remote data analysis server physically located within the first region further comprise:
determining an identifier associated with the de-identified analyzed data from the second region;
determining an association between the identifier and the first patient-identifiable information stored within the first region; and
determining the first patient-identifiable information corresponding to the de-identified analyzed data based on the association between the identifier and the first patient-identifiable information stored within the first region.

16. The system of claim 14, the operations further comprising:
determining, at the remote data analysis server physically located within the first region, a hash associated with the de-identified analyzed data or the de-identified data; and
determining, at the remote data analysis server physically located within the second region, previously analyzed data associated with either the de-identified analyzed data or the de-identified data, based on a comparison of the hash to one or more stored hashes.

17. A non-transitory computer readable medium for use on a computer system containing computer-executable programming instructions that execute operations for processing electronic images while transferring data across regions, the operations comprising:
removing, using a processor physically located in a first region, first patient-identifiable information from patient-specific data to generate a first set of de-identified data, based on a first geographic region specific privacy standard;
storing, using the processor physically located in the first region, the first patient-identifiable information within the first region;
transmitting, using the processor physically located in the first region, the first set of de-identified data to a remote data analysis server physically located in a second region for a patient-specific computation based on the first set of de-identified data;
generating, using the remote data analysis server physically located within the second region, a model of a patient based on the first set of de-identified data and conducting the patient-specific computation through the generated model;
determining, using the remote data analysis server physically located within the second region, a patient-specific blood flow computation in the patient based on the generated model and a mass or a volume of a myocardial tissue of the patient;
receiving, by the processor physically located in the first region, analyzed de-identified data from the remote data analysis server physically located in the second region; and
identifying a patient associated with the generated model by determining, using the processor physically located in the first region, first patient-identifiable information associated with the analyzed de-identified data based on the first patient-identifiable information stored within the first region and the patient-specific blood flow computation stored in a permanent storage at the second geographic region, wherein the first patient privacy information is inaccessible within the second geographic region.

18. The non-transitory computer readable medium of claim 17, wherein the second region is distinct from and outside the first region, and
wherein the first region and the second region are governed by different data anonymization regulations.

19. The non-transitory computer readable medium of claim 17, the operations further comprising:
generating, using a processor physically located in the first region, an identifier associated with the first set of de-identified data, wherein the first patient-identifiable information is absent from the identifier.

20. The non-transitory computer readable medium of claim 17, the operations further comprising:
generating, using a processor physically located in the first region, an irreversible hash of the first patient-identifiable information.

* * * * *